US00PP25857P3

(12) United States Plant Patent

Hansen et al.

(10) Patent No.: US PP25,857 P3

(45) Date of Patent: Sep. 1, 2015

(54) *AGASTACHE* PLANT NAMED 'ROSIE POSIE'

(50) Latin Name: ***Agastache* spp.**
Varietal Denomination: Rosie Posie

(71) Applicants: Hans A. Hansen, Zeeland, MI (US); Kevin A. Hurd, Merrillville, IN (US)

(72) Inventors: Hans A. Hansen, Zeeland, MI (US); Kevin A. Hurd, Merrillville, IN (US)

( * ) Notice: Subject to any disclaimer, the term of this patent is extended or adjusted under 35 U.S.C. 154(b) by 112 days.

(21) Appl. No.: 13/998,865

(22) Filed: Dec. 16, 2013

(65) Prior Publication Data

US 2015/0173287 P1 Jun. 18, 2015

(51) Int. Cl.
*A01H 5/02* (2006.01)

(52) U.S. Cl.
USPC ..... Plt./399

(58) Field of Classification Search
USPC ..... Plt./399
See application file for complete search history.

*Primary Examiner* — Susan McCormick Ewoldt

(57) ABSTRACT

A new and unique cultivar of Hyssop plant, named *Agastache* 'Rosie Posie' with long single reddish-pink to reddish-lavender flowers in tightly clustered verticils. The plant habit is compact and upright with a long bloom time and usefulness in the landscape extended by the persistent and colorful rosie calyxes.

1 Drawing Sheet

Botanical denomination: *Agastache* spp.
Variety designation: 'Rosie Posie'.

BACKGROUND OF THE INVENTION

The present invention relates to the new and distinct plant cultivar of Hyssop or Anise Hyssop from the genus *Agastache* and given the cultivar name 'Rosie Posie' previously known internally by the breeder code HK-10-18-01. The new plant was the result of a planned cross in the summer of 2010 by Kevin A. Hurd and Hans A. Hansen between *Agastache* 'Firebird' (not patented) as the female or seed parent and *Agastache* 'Ava' not patented) in a mixed isolation bed as the male or pollen parent. The seed was collected in September of 2010 and the new hybrid was first isolated from trials at a nursery in Zeeland, Mich. during the summer of 2011 and selected for final introduction in the summer of 2012. *Agastache* 'Rosie Posie' has been asexually propagated at the same nursery in Zeeland, Mich. using traditional shoot tip and stem cutting procedures and found to reproduce plants that are identical and exhibit all the characteristics of the original plant in successive generations of asexual propagation.

The new plant, *Agastache* 'Rosie Posie', has not been observed under all possible environments. The phenotype may vary slightly with different environmental conditions, such as temperature, light, fertility, moisture and maturity levels, but without any change in the genotype.

In comparison to the seed parent, *Agastache* 'Firebird', the new cultivar 'Rosie Posie' has more reddish purple flower petals rather than the bronzy red flower petals. In comparison to the male plant in the isolation bed, *Agastache* 'Ava', the new plant has flowers with slightly less red petals and calyxes with less intense red with a green undertone.

The new plant *Agastache* 'Rosie Posie' is distinct from the parents and all other Hyssop known to the inventors in the following combined traits:

1. Compact upright well-branched habit;
2. Large reddish-pink to reddish-lavender flowers in tightly clustered verticils;

3. Long bloom time with effectiveness extended by persistent rosie-colored calyxes.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, temperature, source and direction may cause the appearance of minor variation in color.

DETAILED PLANT DESCRIPTION

Figure 1:
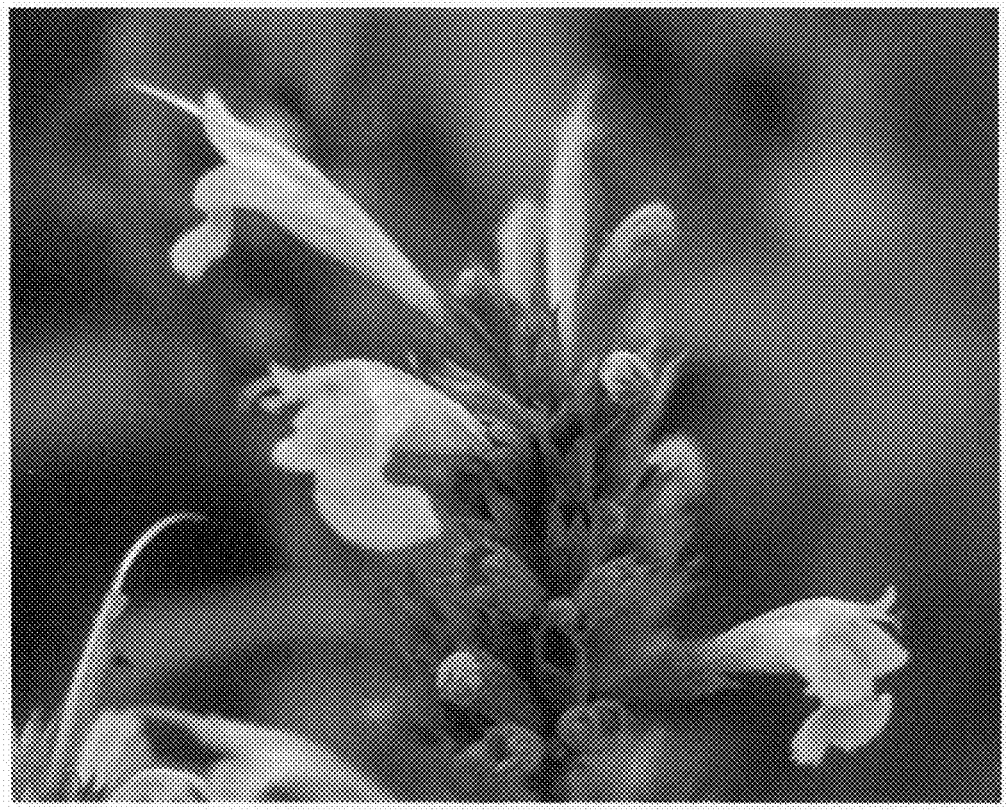
FIG. 1 shows a close-up of the scape with flowers, buds and calyxes.
Figure 2:
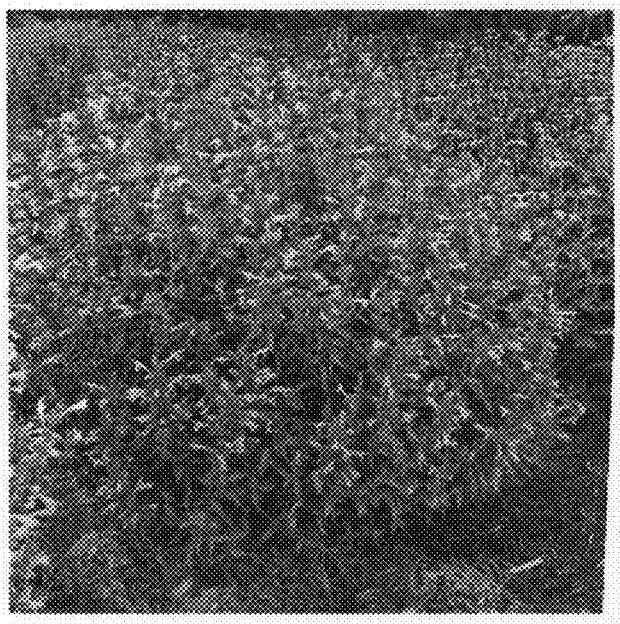
FIG. 2 shows a side view of a two-year old plant in flower in mid-September in a trial block at a nursery in Zeeland, Mich.

The following is a detailed description of the new *Agastache* cultivar "Rosie Posie' based on observations of two-year old specimens grown in outdoor trial beds with supplemental watering and fertilizer as needed at a nursery in Zeeland, Mich. Color descriptions are from the 2001 edition of The Royal Horticultural Society Colour Chart except where common dictionary terms are used.

Plant habit: Herbaceous perennial, upright, heavily branched.

Plant size: 50.0 to 54.0 cm tall and 40.0 to 45.0 cm across.

Roots: Fibrous; to about 2.0 mm diameter near base; color light tan nearest RHS 165D.

Stem: Square in cross-section, stiff, wiry, finely pubescent; averaging about 3.0 mm across at base and 52.0 cm tall with flowering starting about 12.0 cm above soil; internodes vary from 2.0 to 5.0 cm long.

Leaf: Simple, opposite, crenate to serrate; deltoid to ovate, base truncate to rounded with acute apex; blade top and bottom surfaces glabrous; size 3.5 cm to 4.5 cm long and 1.7 to 3.5 cm across.

Leaf venation: Pinnate; glabrous above, pubescent below.

Leaf color: Above nearest RHS 137A, below nearest RHS 137B; veins above the same color as surrounding tissue, below nearest RHS 138B.

Leaf fragrance: Moderately herbal.

Petiole: Minutely pubescent; concavo-convex; 0.5 cm to 2.5 cm long and 1.0 to 1.5 mm across.

Petiole color: Above nearest RHS 137A, below nearest RHS 137B.

Inflorescence: In spikes and whorls of leaf axils and nodes above leaves; 5 to 15 whorls per spike; up to 40 flowers per whorl and 250 per spike.

Bloom period: July through frost in Zeeland, Mich.

Peduncle: Average 52.0 cm tall and 3.0 mm at base; pubescent.

Peduncle color: Between RHS 137B and RHS 138A in lower portion of stem; node color and upper regions of stem become tinted with between RHS 187 B and RHS N187B with denser tinting with more sun exposure.

Flower: Perfect; zygomorphic, tubular, bilabiate; in spikes and whorls in axils of leaves; 5 united sepals, 5-part corolla with 2 lips, upper lip 2-lobed and lower lip 3-lobed; about 2.7 cm long, 7.0 mm tall and 6.0 mm across; each spike flowering for about 3 weeks but remain effective for about 5 weeks or more with strongly pigmented persistent calyxes, individual flowers open for about 3 days.

Petals: Pubescent outside, glabrous inside; upper and lower petals proximally fused to a tube in the basal 16.0 mm.

Upper 2-lobed petal: About 22.0 mm long and 5.0 mm diameter; lobes cleft about 1.5 mm; apex rounded, margin entire.

Lower 3-lobed petal: About 24.0 mm long, bent downward in last 6.0 mm, central lower lip about 4.0 mm wide at base of three lobes reflex downward and flares to about 8.0 mm wide with a rounded apex and serrate margin; two side lobes of lower petal spread horizontally, about 18.0 mm long with obovate apex and entire margin.

Petal color: Abaxial and adaxial sides between RHS N74C and RHS 75A.

Bud on day prior to opening: Club-shaped to obelliptic; about 17.0 mm long, 6.0 mm tall and 4.5 mm wide just before the apex.

Bud color: Between RHS 46A and RHS N34A toward apex, lightening to nearest RHS 45D toward base.

Calyx: Entire, apex acute; base fused into tube; five, fused in basal 6.5 mm and distally separated in the last 1.5 mm; combined about 8.0 mm long and diameter about 2.5 mm; pubescent outside and glabrous inside.

Calyx color: Between RHS 59B and RHS 59C before flower opening, developing between RHS 147B and RHS 147C between the veins two to three weeks after petal dehisces; vein color begins between RHS 59B and RHS 59C before flower opening and develops to nearest RHS 59B with a slight tint of RHS 147C.

Gynoecium:

*Style.*—One, about 20 mm long and 0.5 mm diameter; rounded in cross section.

*Style color.*—Between RHS 75B and RHS 76B before stigma and darkening before stigma split to between RHS 72B and RHS 72C.

*Stigma.*—Split into two and curled back to an angle of about 170 degrees; each segment about 1.0 mm long and less than 0.5 mm diameter; tapering to a pointed apex.

*Stigma color.*—Nearest RHS N77A.

*Ovary.*—Superior; about 0.5 mm diameter.

*Ovary color.*—Between RHS 150D and RHS 150C.

Androecium:

*Stamen.*—Four in two pairs, exerted, adnate to the corolla.

*Filaments.*—Two long about 4 in number, paired and exerted; longer pair fused in the basal 17.0 mm and free in the proximal 8.0 mm; shorter pair fused in the basal 14.0 mm and free in the proximal 8.0 mm.

*Filament color.*—Between RHS 77C and RHS 77D.

*Anthers.*—Dorsifixed, versatile, longitudinal; about 1.0 mm long and 0.5 mm across.

*Anther color.*—Between RHS N186B and RHS N187A.

Fragrance: None detected.

Fruit: Two carpels.

Seed: Nutlet, four, flattened ovoid; about 2.0 mm long, 1.0 mm diameter and 0.5 mm thick.

Seed color: Nearest Black 202A.

Resistance: 'Rosie Posie' is resistant to deer browsing but has not been tested or shown resistance to other pests and diseases common to *Agastache*. The new plant has survived USDA hardiness zones 7 to 10 but has not been tested yet beyond these temperatures.

We claim:

1. The new and distinct plant cultivar *Agastache* 'Rosie Posie' as herein described and photographed, with compact upright habit, large reddish pink to reddish lavender flowers in tightly clustered verticils, and long bloom time, effective for landscaping and attracting butterflies and hummingbirds as well as for cut flowers.

* * * * *